(12) United States Patent
Abbitt et al.

(10) Patent No.: US 7,211,712 B2
(45) Date of Patent: May 1, 2007

(54) SEED-PREFERRED REGULATORY ELEMENTS

(75) Inventors: Shane E. Abbitt, Ankeny, IA (US); Rudolf Jung, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/284,201

(22) Filed: Nov. 21, 2005

(65) Prior Publication Data

US 2006/0130184 A1    Jun. 15, 2006

Related U.S. Application Data

(60) Provisional application No. 60/634,914, filed on Dec. 10, 2004.

(51) Int. Cl.
*C12P 7/62* (2006.01)
*C12P 11/00* (2006.01)
*C07H 21/04* (2006.01)
*A01H 1/00* (2006.01)

(52) U.S. Cl. .................. 800/295; 435/6; 435/69.1; 435/320.1; 435/410; 435/419; 435/468; 536/24.1; 800/287; 800/312

(58) Field of Classification Search ............... 800/287, 800/320.1, 320.3; 435/320.1, 419, 468; 536/24.1
See application file for complete search history.

(56) References Cited

OTHER PUBLICATIONS

Hannenhalli et al., (2001) Promoter prediction in the human genome. Bioinformatics 17: S90-S96.*
Kim et al., (1994) A 20 nucleotide upstream element is essential for the nopaline synthase (nos) promoter activity. Plant Molecular Biology 24: 105-117.*

* cited by examiner

*Primary Examiner*—Phuong Bui
*Assistant Examiner*—Brendan O. Baggot
(74) *Attorney, Agent, or Firm*—Pioneer Hi-Bred International, Inc.; Kathryn K. Lappegard

(57) ABSTRACT

The present invention provides compositions and methods for regulating expression of heterologous nucleotide sequences in a plant. Compositions are novel nucleotide sequences for a seed-preferred promoter and terminator isolated from the maize legumin 1 coding region. A method for expressing a heterologous nucleotide sequence in a plant using the regulatory sequences disclosed herein is provided. The method comprises transforming a plant cell to comprise a heterologous nucleotide sequence operably linked to one or more of the regulatory sequences of the present invention and regenerating a stably transformed plant from the transformed plant cell.

6 Claims, No Drawings

SEED-PREFERRED REGULATORY ELEMENTS

CROSS REFERENCE TO RELATED APPLICATIONS

This application claims the benefit of U.S. Application Ser. No. 60/634,914 filed Dec. 10, 2004, which is herein incorporated in its entirety by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs are desired, tissue-specific promoters may be used. That is, they may drive expression in specific tissues or organs. Such tissue-specific promoters may be temporally constitutive or inducible. In either case, additional regulatory sequences upstream and/or downstream from a core promoter sequence may be included in expression constructs of transformation vectors to bring about varying levels of expression of heterologous nucleotide sequences in a transgenic plant.

As this field develops and more genes become accessible, a greater need exists for transformed plants with multiple genes. These multiple exogenous genes typically need to be controlled by separate regulatory sequences however. Further, some genes should be regulated constitutively whereas other genes should be expressed at certain developmental stages or locations in the transgenic organism. Accordingly, a variety of regulatory sequences having diverse effects is needed.

Diverse regulatory sequences are also needed as undesirable biochemical interactions can result from using the same regulatory sequence to control more than one gene. For example, transformation with multiple copies of a regulatory element may cause: homologous recombination between two or more expression systems; formation of hairpin loops caused from two copies of the same promoter or enhancer in opposite orientation in close proximity; competition between identical expression systems for binding to common promoter-specific regulatory factors; or inappropriate expression levels of an exogenous gene due to trans effects of a second promoter or enhancer.

Isolation and characterization of seed-preferred promoters and terminators that can serve as regulatory elements for expression of isolated nucleotide sequences of interest in a seed-preferred manner are needed for improving seed traits in plants.

In view of these considerations, a goal in this field has been the discovery and construction of new regulatory sequences for transgenic control of DNA constructs.

DETAILED DESCRIPTION OF THE INVENTION

In accordance with the invention, nucleotide sequences are provided that allow regulation of transcription in seed. The sequences of the invention comprise transcriptional initiation and termination regions associated with seed formation and seed tissues. Thus, the compositions of the present invention comprise novel nucleotide sequences for plant regulatory elements natively associated with the nucleotide sequences coding for *Zea mays* legumin 1.

A method for expressing an isolated nucleotide sequence in a plant using the regulatory sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a seed-preferred manner.

Under the regulation of the seed-specific regulatory elements will be a sequence of interest, which will provide for modification of the phenotype of the seed. Such modification includes modulating the production of an endogenous product, as to amount, relative distribution, or the like, or production of an exogenous expression product to provide for a novel function or product in the seed.

Definitions

By "seed-preferred" is intended favored expression in the seed, including but not limited to, at least one of embryo, kernel, pericarp, endosperm, nucellus, aleurone, pedicel, and the like.

By "regulatory element" is intended sequences responsible for tissue and temporal expression of the associated coding sequence including promoters, terminators, enhancers, introns, and the like.

By "terminator" is intended sequences that are needed for termination of transcription: a regulatory region of DNA that causes RNA polymerase to disassociate from DNA, causing termination of transcription.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

The isolated promoter sequence of the present invention can be modified to provide for a range of expression levels of the isolated nucleotide sequence. Less than the entire promoter region can be utilized and the ability to drive seed-preferred expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art. One method is described in U.S. patent application Ser. No. 06/098,690 filed Aug. 31, 1998, herein incorporated by reference. The sequence for the promoter region is set forth in SEQ ID NO:1.

The Leg1 promoter set forth in SEQ ID NO:1 is 1070 nucleotides in length. The Leg1 promoter was isolated using the *Zea mays* legumin 1 coding region represented by SEQ ID NO:4 (Woo et al., Plant Cell, 2001; 13(10):2297–2317). It was isolated based on MPSS (Massively Parallel Signature Sequencing) technology from LYNX™ (see Brenner et al, Nature Biotechnology 18:630–634, 2000) expression analysis showing strong expression in 8–40 DAP (days after pollination) maize endosperm. The Leg1 promoter can address expression problems by providing this pattern of expression in developing maize kernels.

The following cis elements are found in the Leg1 promoter:

AACA motif: Core AACA motif found in rice (*Oryza sativa*) glutelin genes, involved in controlling endosperm-specific expression. AACA is also closely associated with the GCN4 motif in all rice glutelin genes and together they have been shown to confer endosperm-specific enhancement to the truncated –90 CaMV 35S promoter. (see Wu et. al., Plant J., 2000 Aug; 23(3):415–21). This motif is located from positions 696–703 of SEQ ID NO:1.

CAAACAC element: Conserved in many storage-protein gene promoters; may be important for high activity of the napA promoter. (see Stalberg et al., Planta, 1996; 199(4): 515–9). This element is located from positions 937–941 of SEQ ID NO:1.

AAAG motif: Core site required for binding of Dof proteins in maize (*Z. mays*); Dof proteins are DNA binding proteins, with presumably only one zinc finger, and are unique to plants. Four cDNAs encoding Dof proteins: Dof1, Dof2, Dof3 and PBF, have been isolated from maize. PBF is an endosperm specific Dof protein that binds to prolamin boxes; maize Dof1 enhances transcription from the promoters of both cytosolic orthophosphate kinase (CyPPDK) and a non-photosynthetic PEPC gene; maize Dof2 suppressed the C4PEPC promoter. (see Yanagisawa S, and R J Schmidt, Plant J., 1999 Jan; 17(2):209–14.) There are three of these binding sites found in the Leg1 promoter: positions 301–310, 881–884 and 886–889 of SEQ ID NO:1.

The promoter regions of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, and sorghum.

Promoter sequences from other plants may be isolated according to well-known techniques based on their sequence homology to the promoter sequences set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

The Leg1 promoter of the present invention includes variations from the native promoter at positions 1067 (A to T) and 1070 (A to C). These variants were created by site-directed mutagenesis to introduce Eco47III and NcoI restriction sites to facilitate cloning.

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Zhu et al., The Plant Cell 7:1681–89 (1995). Such variants should retain promoter activity, particularly the ability to drive expression in seed or seed tissues. Activity can be measured by Northern blot analysis, reporter activity measurements when using transcriptional fusions, and the like. See, for example, Sambrook et al. (1989) Molecular Cloning: A Laboratory Manual (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) Methods Enzymol. 155:335–350, and Erlich, ed. (1989) PCR Technology (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The Leg1 promoter of the present invention includes the functional fragment ZM-Leg1B (SEQ ID NO:2) created by isolating the fragment from B73 genomic DNA using the primers represented by SEQ ID NOS:8 and 9.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) PCR Protocols, A Guide to Methods and Applications, eds., Academic Press).

The seed-preferred regulatory elements disclosed in the present invention, as well as variants and fragments thereof, are useful in the genetic manipulation of any plant when operably linked with an isolated nucleotide sequence of interest whose expression is to be controlled to achieve a desired phenotypic response. By "operably linked" is intended the transcription or translation of the isolated nucleotide sequence of interest under the influence of the regulatory sequence.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994 herein incorporated in it's entirety by reference.

The regulatory elements of the invention can be operably linked in expression cassettes along with isolated nucleotide sequences of interest for expression in the desired plant, more particularly in the seed of the plant. Such an expression cassette is provided with a plurality of restriction sites for insertion of the nucleotide sequence of interest under the transcriptional control of the regulatory elements.

The isolated nucleotides of interest expressed by the regulatory elements of the invention can be used for varying the phenotype of seeds. This can be achieved by increasing expression of endogenous or exogenous products in seeds. Alternatively, the results can be achieved by providing for a reduction of expression of one or more endogenous products, particularly enzymes or cofactors in the seed. These modifications result in a change in phenotype of the transformed seed. It is recognized that the regulatory elements may be used with their native coding sequences to increase or decrease expression resulting in a change in phenotype in the transformed seed.

General categories of genes of interest for the purposes of the present invention include for example, those genes involved in information, such as Zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

It is recognized that any gene of interest, including the native coding sequence, can be operably linked to the regulatory elements of the invention and expressed in the seed.

Modifications that affect grain traits include increasing the content of oleic acid, or altering levels of saturated and unsaturated fatty acids. Likewise, the level of seed proteins, particularly modified seed proteins that improve the nutrient value of the seed, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997; the disclosures of which are incorporated herein by reference. Another example is lysine and/or sulfur-rich seed protein encoded by the soybean 2S albumin described in WO 9735023 filed Mar. 20, 1996, and the chymotrypsin inhibitor from barley, Williamson et al. (1987) Eur. J. Biochem. 165:99–106, the disclosures of each are incorporated by reference.

Agronomic traits in seeds can be improved by altering expression of genes that: affect the response of seed growth and development during environmental stress, Cheikh-N et al (1994) Plant Physiol. 106(1):45–51) and genes controlling carbohydrate metabolism to reduce kernel abortion in maize, Zinselmeier et al. (1995) Plant Physiol. 107(2):385–391.

Insect resistance genes may encode resistance to pests that have great yield drag such as rootworm, cutworm, European Corn Borer, and the like. Such genes include, for example: *Bacillus thuringiensis* endotoxin genes, U.S. Pat. Nos. 5,366,892; 5,747,450; 5,737,514; 5,723,756; 5,593,881; Geiser et al. (1986) Gene 48:109; lectins, Van Damme et al. (1994) Plant Mol. Biol. 24:825; and the like.

Genes encoding disease resistance traits include: detoxification genes, such as against fumonosin (WO 9606175 filed Jun. 7, 1995); avirulence (avr) and disease resistance (R) genes, Jones et al. (1994) Science 266:789; Martin et al. (1993) Science 262:1432; Mindrinos et al. (1994) Cell 78:1089; and the like.

Commercial traits in plants can be created through the expression of genes that alter starch or protein for the production of paper, textiles, ethanol, polymers or other materials with industrial uses.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant seed.

The expression cassette will also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

The Leg1 terminator set forth in SEQ ID NO:3 is 780 nucleotides in length. The terminator was isolated using a coding sequence found in maize tissue libraries of 18 to 40 DAP (days after pollination) endosperm tissue. The coding region was identified according to the procedure described in Woo et al, Journal Plant Cell 13(10), 2297–2317 (2001) incorporated herein by reference. The terminator can be isolated with the primers/probes of SEQ ID NOS:10 and 11. The Leg 1 terminator, with the appropriate promoter, can provide expression during 840 DAP development. The Leg1 terminator can be used with the Leg1 promoter in an expression cassette, or can be used with another appropriate promoter to provide seed-preferred expression of a coding region.

Other convenient termination regions are available from the Ti-plasmid of *A. tumefaciens*, such as the octopine synthase and nopaline synthase termination regions. See also: Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. 1989) Nucleic Acids Res. 17:7891–7903; Joshi et al. (1987) Nucleic Acid Res. 15:9627–9639.

The expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein et al. (1989) Proc. Natl. Acad. Sci. USA 86:6126–6130; potyvirus leaders, for example, TEV leader (Tobacco Etch Virus), Allison et al. (1986); MDMV leader (Maize Dwarf Mosaic Virus), Virology 154:9–20; human immunoglobulin heavy-chain binding protein (BiP), Macejak et al. (1991) Nature 353: 90–94; untranslated leader from the coat protein mRNA of alfalfa mosaic virus (AMV RNA 4), Jobling et al. (1987) Nature 325:622–625); tobacco mosaic virus leader (TMV), Gallie et al. (1989) Molecular Biology of RNA, pages 237–256; and maize chlorotic mottle virus leader (MCMV), Lommel et al. (1991) Virology 81:382–385. See also Della-Cioppa et al. (1987) Plant Physiology 84:965–968. The cassette can also contain sequences that enhance translation and/or mRNA stability such as introns.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson et al. (1991) in Plant Molecular Biology Manual, ed. Gelvin et al. (Kluwer Academic Publishers), pp. 1–33; DeWet et al. (1987) Mol. Cell. Biol. 7:725–737; Goff et al. (1990) EMBO J. 9:2517–2522; Kain et al. (1995) BioTechniques 19:650–655; and Chiu et al. (1996) Current Biology 6:325–330.

Selectable marker genes for selection of transformed cells or tissues can be included in the transformation vectors.

These can include genes that confer antibiotic resistance or resistance to herbicides. Examples of suitable selectable marker genes include, but are not limited to: genes encoding resistance to chloramphenicol, Herrera Estrella et al. (1983) EMBO J. 2:987–992; methotrexate, Herrera Estrella et al. (1983) Nature 303:209–213; Meijer et al. (1991) Plant Mol. Biol. 16:807–820; hygromycin, Waldron et al. (1985) Plant Mol. Biol. 5:103–108; Zhijian et al. (1995) Plant Science 108:219–227; streptomycin, Jones et al. (1987) Mol. Gen. Genet. 210:86–91; spectinomycin, Bretagne-Sagnard et al. (1996) Transgenic Res. 5:131–137; bleomycin, Hille et al. (1990) Plant Mol. Biol. 7:171–176; sulfonamide, Guerineau et al. (1990) Plant Mol. Biol. 15:127–136; bromoxynil, Stalker et al. (1988) Science 242:419–423; glyphosate, Shaw et al. (1986) Science 233:478–481; phosphinothricin, DeBlock et al. (1987) EMBO J. 6:2513–2518.

Other genes that could serve utility in the recovery of transgenic events but might not be required in the final product would include, but are not limited to: GUS (β-glucoronidase), Jefferson (1987) Plant Mol. Biol. Rep. 5:387); GFP (green florescence protein), Chalfie et al. (1994) Science 263:802; luciferase, Teeri et al. (1989) EMBO J. 8:343; and the maize genes encoding for anthocyanin production, Ludwig et al. (1990) Science 247:449.

A transformation vector comprising the particular regulatory sequences of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) Biotechniques 4:320–334; electroporation, Riggs et al. (1986) Proc. Natl. Acad. Sci. USA 83:5602–5606; Agrobacterium-mediated transformation, see for example, Townsend et al. U.S. Pat. No. 5,563,055; direct gene transfer, Paszkowski et al. (1984) EMBO J. 3:2717–2722; and ballistic particle acceleration, see for example, Sanford et al. U.S. Pat. No. 4,945,050; Tomes et al. (1995) in Plant Cell, Tissue, and Organ Culture: Fundamental Methods, ed. Gamborg and Phillips (Springer-Verlag, Berlin); and McCabe et al. (1988) Biotechnology 6:923–926. Also see Weissinger et al. (1988) Annual Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Klein et al. (1988) Plant Physiol. 91:440–444 (maize); Fromm et al. (1990) Biotechnology 8:833–839; Hooydaas-Van Slogteren et al. (1984) Nature (London) 311:763–764; Bytebier et al. (1987) Proc. Natl. Acad. Sci. USA 84:5345–5349 (Liliaceae); De Wet et al. (1985) in The Experimental Manipulation of Ovule Tissues, ed. G. P. Chapman et al. (Longman, N.Y.), pp. 197–209 (pollen); Kaeppler et al. (1990) Plant Cell Reports 9:415–418; and Kaeppler et al. (1992) Theor. Appi. Genet. 84:560–566 (whisker-mediated transformation); D. Halluin et al. (1992) Plant Cell 4:1495–1505 (electroporation); Li et al. (1993) Plant Cell Reports 12:250–255 and Christou et al. (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed can be grown into plants in accordance with conventional ways. See, for example, McCormick et al. (1986) Plant Cell Reports 5:81–84. These plants can then be grown and pollinated with the same transformed strain or different strains. The resulting hybrid having seed-preferred expression of the desired phenotypic characteristic can then be identified. Two or more generations can be grown to ensure that seed-preferred expression of the desired phenotypic characteristic is stably maintained and inherited.

The following examples are offered by way of illustration and not by way of limitation.

EXAMPLES

Regulatory regions from maize Leg1 (legumin 1) were isolated from maize plants and cloned. Maize Leg1 was selected as a source of seed-preferred regulatory elements based on the spatial and temporal expression of its products. The method for their isolation is described below.

Example 1

Prediction of Expression Via Lynx MPSS

Lynx™ gene expression profiling technology was used to identify the maize Leg1 coding region as a candidate for promoter isolation. Massively parallel signature sequencing (MPSS, see Brenner et al, Nature Biotechnology 18:630–634, 2000) indicated expression of about 5K ppm beginning at 10 DAP in endosperm, peaking at about 23k ppm at 21 DAP and tapering off to less than 5K ppm at 40 DAP. Expression of from about 3–4k ppm was also present in 15–27 DAP pericarp. MPSS data showed very low expression of maize Leg1 in flowering or vegetative tissue.

Example 2

Prediction of Expression Pattern Via RT PCR

RT-PCR was performed on maize whole kernels from 1–46 DAP as well as pooled embryo, endosperm, pericarp, leaf, shoot, root, and anther tissue.

Results as shown by gel electrophoresis agreed with the MPSS data. The maize Leg1 transcript was present from 10–40 DAP in endosperm and pericarp tissues. It was not present in any vegetative or flowering tissues.

Example 3

Isolation of Regulatory Sequences using Genome Walker

The procedure for promoter isolation is described in the User Manual for the Genome Walker kit sold by Clontech Laboratories, Inc., Palo Alto, Calif. Genomic DNA from maize line V3-4 A63 was prepared by grinding 10-day-old seedling leaves in liquid nitrogen, and the DNA prepared as described by Chen and Dellaporta (1994) in The Maize Handbook, ed. Freeling and Walbot (Springer-Verlag, Berlin) with a few minor modifications as follows: precipitated DNA was recovered using an inoculation loop and transferred to a 1.5 ml eppendorf tube containing 500 μl of TE(10 mM Tris pH 8.0, 1 mM EDTA). The DNA was allowed to dissolve at room temperature for 15 minutes, phenol extracted and 2-propanol precipitated in 700 μl. The precipitate was recovered and washed with 70% ethanol. The DNA was then placed in a clean 1.5 ml eppendorf tube to air dry and resuspended in 200 μl of TE. RNase A was added to 10 μg/ml and the mixture was incubated at 37° C. for several hours. The DNA was then extracted once with phenol-chloroform, then chloroform, then ethanol precipitated and resuspended in TE. The DNA was then used as described in the Genome Walker User Manual (Clontech PT3042-1 version PR68687) with the following modifications: briefly, the DNA was digested separately with restriction enzymes DraI, EcoRV, PvuII, ScaI, StuI, HpaI, EcoICRI, XmnI, and SspI all blunt-end cutters, creating nine "libraries" of genomic DNA. The DNA was extracted with phenol, then chloroform, then ethanol precipitated. The Genome Walker adapters were ligated onto the ends of the restricted DNA. The resulting samples were referred to as DL1-9 respectively.

The ZM-LEG1 PRO was isolated from B73 genomic DNA using two nonoverlapping gene-specific primers (SEQ ID NOS:12 and 13) designed from the 5' end of the maize leg1 coding sequence to produce a 1086 bp fragment. The first round of PCR was performed on each DNA sample (DL1-9) with Clontech primer AP1 and the gene-specific primer 1 (gsp1) represented by SEQ ID NO:12.

PCR was performed in a Bio-Rad icycler (Hercules, Calif.) thermal cycler using reagents supplied with the Genome Walker kit. The following cycle parameters were used: 7 cycles of 94° C. for 2 seconds, then 70° C. for 3 minutes, followed by 36 cycles of 94° C. for 2 seconds and 67° C. for 3 minutes. Finally, the samples were held at 67° C. for 4 minutes and then at 4° C. until further analysis.

As described in the User Manual, the DNA from the first round of PCR was then diluted and used as a template in a second round of PCR using the Clontech AP2 primer and gene-specific primer 2 (gsp2) represented by SEQ ID NO:13.

The cycle parameters for the second round were: 5 cycles of 94° C. for 2 seconds, then 70° C. for 3 minutes, followed by 25 cycles of 94° C. for 2 seconds and 67° C. for 3 minutes. Finally, the samples were held at 67° C. for 4 minutes and then held at 4° C. Approximately 10 μl of each reaction were run on a 0.8% agarose gel, and bands (usually 500 bp or larger) were excised, purified with the Qiagen Gel Extraction Kit (Santa Clarita, Calif.) and cloned into the pGEM-T Easy vector (Promega Corp. Madison, Wis.). Clones were sequenced for verification.

After verification that the amplified sequence was from the region of genomic DNA upstream of the Legumin1 coding region, the ZM-LEG1 promoter region was isolated with two variations, which differed only in the amount of upstream sequence which they contained. Both promoters were re-isolated by amplifying new fragments from genomic DNA from maize line V3-4 A63 using primers created from the new promoter sequence using SEQ ID NOS:6 and 7 as primers to amplify the full length version, and SEQ ID NOS:7 and 8 as primers for a truncated version. This was done to insure that sequences were error free and to add restriction sites to facilitate vector construction. The truncated version (ZM-LEG1B PRO) deletes an upstream region containing several CAAT and TATA sequences.

The PCR reaction was performed in a Bio-Rad icycler (Hercules, Calif.) thermal cycler using Hifidelity supermix (Cat.# 10790-020, Life Technologies, Rockville Md.). The following cycle parameters were used: 94° C. for 2 seconds, followed by 30 cycles of 94° C. for 20 seconds, for 30 seconds, and 68° C. for 1 minute. Finally, the samples were held at 67° C. for 4 minutes and then at 4° C. until further analysis.

The PCR products were cloned into the (Promega®) pGEM-easy vector and sequenced using M13F and M13R primers. Upon sequence verification, they were given PHP numbers and archived: PHP18850 (ZM-LEG1 PRO), and PHP18851 (ZM-LEG1B PRO).

The Zm-Leg1 terminator was isolated essentially as above using primers designed from the 3' end of the Leg1 coding region using the gene specific primers represented by SEQ ID NOS:14 and 15. Once verified, the terminator was then re-isolated from B73 genomic DNA using primers based on the new sequence (SEQ ID NO:10 and 11) to add restriction enzyme sites. The 780 bp fragment cloned into the Promega® pGEM-easy vector and sequence confirmed using M13F and M13 R primers. This vector was archived as PHP18968.

Example 4

Expression Data Using ZM-Leg1 Regulatory Sequences

Two promoter::GUS::terminator fusion constructs were prepared by the methods described below. All vectors were constructed using standard molecular biology techniques (Sambrook et al., Supra).

ZM-Leg1 Pro: GUSINT:ZM-Leg1 Term
ZM-Leg1B Pro: GUSINT:ZM-Leg1 Term

A reporter gene and a selectable marker gene for gene expression and selection was inserted between the multiple cloning sites of the pBluescript cloning vector (Stratagene Inc., 11011 N. Torrey Pines Rd., La Jolla, Calif.). The reporter gene was the β-glucuronidase (GUS) gene (Jefferson, R. A. et al., 1986, Proc. Natl. Acad. Sci. USA 83:8447–8451) into whose coding region was inserted the second intron from the potato ST-LS1 gene (Vancanneyt et al., Mol. Gen. Genet. 220:245–250, 1990), to produce GUS-INT, in order to prevent expression of the gene in *Agrobacterium* (see Ohta, S. et al., 1990, Plant Cell Physiol. 31(6): 805–813.

Successful subcloning was confirmed by restriction analysis.

The *Agrobacterium* transformation plasmids were constructed by inserting the GUS expression cassettes as BstEII fragments into a descendent plasmid of pSB11 which contained the BAR expression cassette (E35SPRO: BAR: PinII) for selection. Both the GUS and BAR expression cassettes were located between the right and left T-DNA. The GUS cassette was inserted proximal to the right T-DNA border. The plasmid pSB 11 was obtained from Japan Tobacco Inc. (Tokyo, Japan). The construction of pSB11 from pSB21 and the construction of pSB21 from starting vectors is described by Komari et al. (1996, Plant J. 10:165–174). The T-DNA of the plasmid was integrated into the superbinary plasmid pSB1 (Saito et al., EP 672 752 A1) by homologous recombination between the two plasmids. The plasmid pSB1 was also obtained from Japan Tobacco Inc.

Competent cells of the *Agrobacterium* strain LBA4404 harboring pSB1 were created using the protocol as described by Lin (1995) in Methods in Molecular Biology, ed. Nickoloff, J. A. (Humana Press, Totowa, N.J.) The plasmid containing the expression cassettes was electroporated into competent cells of the *Agrobacterium* strain LBA4404 harboring pSB1 to create the cointegrate plasmid in *Agrobacterium* using a BIO-RAD Micropulser (Cat# 165-2100, Hercules, Calif.). Electroporation was performed by mixing 1 ul of plasmid DNA (~100 ng) with 20 μl of competent *Agrobacterium* cells in a 0.2 cm electrode gap cuvette (Cat#

165-2086, BIO-RAD, Hercules, Calif.). Electroporation was performed using the EC2 setting, which delivers 2.5 kV to the cells. Successful recombination was verified by restriction analysis of the plasmid after transformation of the cointegrate plasmid back into E. coli DH5a cells.

Example 5

Transformation and Regeneration of Maize Callus Via *Agrobacterium* Preparation of *Agrobacterium* Suspension

*Agrobacterium* was streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH$_2$O (stock solution A: K2HPO4 60.0 g/l, NaH2PO4 20.0 g/l, adjust pH to 7.0 w/KOH and autoclaved; stock solution B: NH4Cl 20.0 g/l,
MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and autoclaved).

The plate can be stored at 4° C. and used usually for about 1 month. A single colony was picked from the master plate and streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2,4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy4'-hydroxyacetophenone, Aldrich chemicals) were added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobacterium* suspension was aliquoted into 2 ml microcentrifuge tubes, each containing 1 ml of the suspension. The suspensions were then used as soon as possible.

Embryo Isolation, Infection and Co-cultivation:

About 2 ml of the same medium (here PHI-A or PHI-I) used for the 30 *Agrobacterium* suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0–1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension added to the embryos and the tube vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine-.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3–5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli were then "bulked up" by growing on the same medium for another two weeks until the diameter of the calli was about 1.5–2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1–3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m–2 sec–1) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+ events are determined at the callus stage or regenerated plant stage.

For Hi-II, an optimized protocol was: 0.5×109 cfu/ml *Agrobacterium*, a 3–5 day resting step, and no AgNO3 in the infection medium (PHI-A medium).

Example 6

Confirmation of Expression by GUS Assay

Ability of the ZM-LEG1 and Zm-LEG1B promoter and to drive expression in maize endosperm from 10–40 DAP were confirmed by histochemical localization of GUS activity in transgenic kernels using the method of Topping and Lindsey (Plant Molecular Biology—A Laboratory Manual, M. S. Clark (ed), Springer-Verlag, 1997, pp 436–438). No expression was detected in leaf tissue of the same plants.

Although the foregoing invention has been described in some detail by way of illustration and example for purposes of clarity of understanding, it will be obvious that certain changes and modifications may be practiced within the scope of the appended claims.

What is claimed is:

1. An isolated promoter that drives transcription in a seed endosperm-preferred manner, wherein said promoter comprises a nucleotide sequence selected from the group consisting of:
   a) the nucleotide sequence set forth in SEQ ID NO: 1; and
   b) a sequence comprising a functional fragment of the nucleotide sequence set forth in SEQ ID NO: 1.

2. An expression cassette comprising a promoter and a nucleotide sequence operably linked to the promoter, wherein the promoter initiates seed-endosperm preferred transcription of the nucleotide sequence in a plant cell, wherein the promoter comprises a sequence selected from the group consisting of:
   a) the nucleotide sequence set forth in SEQ ID NO: 1; and
   b) a sequence comprising a functional fragment of the nucleotide sequence set forth in SEQ ID NO: 1.

3. A plant stably transformed with an expression cassette comprising a promoter and a nucleotide sequence operably linked to the promoter, wherein the promoter is capable of initiating seed-endosperm preferred transcription of the nucleotide sequence in a plant cell, wherein the promoter comprises a sequence selected from the group consisting of:
   a) the nucleotide sequence set forth in SEQ ID NO: 1; and
   b) a sequence comprising a functional fragment of the nucleotide sequence set forth in SEQ ID NO: 1.

4. The plant of claim 3, wherein said plant is a monocot.

5. The plant of claim 4, wherein said monocot is maize, wheat, rice, barley, sorghum, or rye.

6. Transformed seed of the transformed plant of claim 3.

* * * * *

SEQUENCE LISTING

```
<160> NUMBER OF SEQ ID NOS: 15

<210> SEQ ID NO 1
<211> LENGTH: 1070
<212> TYPE: DNA
<213> ORGANISM: Zea mays
<220> FEATURE:
<221> NAME/KEY: promoter
<222> LOCATION: (1)...(1070)

<400> SEQUENCE: 1
gagtcaggtc aacttggcca aacttaaact gtctcggctc gatatattaa ggaaccgaat      60
aagagaacca actcgtctca tttgtgagtt cgagctctcc cgagctaaaa aaacaatata     120
cacatatata aaatagtata accaattatt agttaattct agacctattt aacactaaaa     180
aagagtaaca atactcacac tttcacatat catgtcaata taacaccaaa ttaacaaatc     240
acttattaat tcatccaaca caagtgcgag atttgttttt ctgacaaatg gttgctcatt     300
caagctaaag agctgactcg aacacagctc gagctggctt gttaacaaat cttgctgaga     360
tactagctca gctcgtgaca aaatcaaaat gagctgagct gaattgagtc gagctaacca     420
tgaaccgagc gatctcacga gccacgagta ttttgtctag tcctaccaaa aagaccggtc     480
cattcttcta gtactagtcc gaaccccgaa aactttatga tttccatagc atttgtcaag     540
gctgcctcat taatcatttt gttgacgatc tagagtactc tagcgaaaac atgcaagcaa     600
ccaaaccgta gagaagtgta gtaggcaagg ctggtcgcta atgcgtgcac ctggacagtc     660
gtaatcggac tgtgcgtgaa cgaactaaaa aggcgcaaca aactgttgga gtcgctagtc     720
agtacaaaac tgaagcggcc tttgcccttt tgtgactgtc agcacaagca acaagtccaa     780
actgttgagc acacgatcca tccaagtcga catcctactg ctgatcgatc gcgagcttgt     840
caggttcttc ccatccaacg tgcacagctc ctatcacggc aaagcaaagc accagcagcg     900
tacgaggaca aggcctgaat ttgttcccag gtgcaacaaa cacttttgt tcttttagc      960 tttgcatcct tctcgttcca cttacttaat ggcacaccat cagcaatgca caccacggca    1020
acagcattca ctgccaagag agtgagcgag cgagcagagg cagcgcagca                1070

<210> SEQ ID NO 2
<211> LENGTH: 800
```

```
<212> TYPE: DNA
<213> ORGANISM: Zea mays
<220> FEATURE:
<221> NAME/KEY: promoter
<222> LOCATION: (1)...(800)
<223> OTHER INFORMATION: truncated promoter

<400> SEQUENCE: 2
atttgttttt ctgacaaatg gttgctcatt caagctaaag agctgactcg aacacagctc      60
gagctggctt gttaacaaat cttgctgaga tactagctca gctcgtgaca aaatcaaaat     120
gagctgagct gaattgagtc gagctaacca tgaaccgagc gatctcacga gccacgagta     180
ttttgtctag tcctaccaaa agaccggtc cattcttcta gtactagtcc gaaccccgaa      240
aactttatga tttccatagc atttgtcaag gctgcctcat taatcatttt gttgacgatc     300
tagagtactc tagcgaaaac atgcaagcaa ccaaaccgta gagaagtgta gtaggcaagg     360
ctggtcgcta atgcgtgcac ctggacagtc gtaatcggac tgtgcgtgaa cgaactaaaa     420
aggcgcaaca aactgttgga gtcgctagtc agtacaaaac tgaagcggcc tttgcccttt     480
tgtgactgtc agcacaagca acaagtccaa actgttgagc acgatcca tccaagtcga      540 catcctactg ctgatcgatc gcgagcttgt caggttcttc ccatccaacg tgcacagctc     600
ctatcacggc aaagcaaagc accagcagcg tacgaggaca aggcctgaat tgttcccag     660 gtgcaacaaa cacttttttgt tcttttttagc tttgcatcct tctcgttcca cttacttaat     720
ggcacaccat cagcaatgca caccacggca acagcattca ctgccaagag agtgagcgag     780
cgagcagagg cagcgcagca                                                800

<210> SEQ ID NO 3
<211> LENGTH: 780
<212> TYPE: DNA
<213> ORGANISM: Zea mays
<220> FEATURE:
<221> NAME/KEY: terminator
<222> LOCATION: (1)...(780)

<400> SEQUENCE: 3
gcacaacctc agagtgatct gcctgaataa gtactcgtag actgtaataa ttaaacaaag      60
cttgctcatg gttaaactgc gtgttgatta gtctttcaac tacatagctc taaagttttt     120
gatacaccga gtgatttgcc aggaaaaaaa tgagcagatt gttgtaagca aaacatgttt     180
gttatggcta aactgcatgt ctacctggat ttgtattttt tttcaactac ctagttcatc     240
tgataaaaac aatttagttg agtaacatac taacatttca aatgaaaatt tattccaagg     300
caaacatatc caaactatct aaaatacatg tggctctgga agataggga gtgaaagcat      360 ttaggagcag gtaactgagt acaatatatc catgcaccat ctgaatgaac tactacctaa     420
ggttaaagct tgaacttccc catgactgca ttgaaactaa aggacaacag atcaccctca     480
tatatctaca tatccaaacc taaataaagg tcaatcttca tctggtgttt cctcatcgtc     540
atcattgttg ccatatctcc agccatcttc aatgttgttg cctccatctt cttccgtctc     600
ttcactatca tcttggtacg tagctttacc tggccactgg ttcctgacgc caatgtcaga     660
aggcattgct ctcgaaacct tggcattgta ggctttggat gagtggacct tgtgcccatg     720
attcgtcttg ctccttttgg ggtttggtgc aatctcgcca acctcggcat agttatactg     780

<210> SEQ ID NO 4
<211> LENGTH: 1654
<212> TYPE: DNA
<213> ORGANISM: Zea mays
```

```
<220> FEATURE:
<221> NAME/KEY: CDS
<222> LOCATION: (34)...(1482)
<223> OTHER INFORMATION: Leg1 coding sequence

<400> SEQUENCE: 4
gcacgaggag cgagcgagca gaggcagcgc aca atg gcg gcg gca ata gta ctc         54
                                    Met Ala Ala Ala Ile Val Leu
                                     1               5 tcc ggc cag gtg cgg ccg ctt ccc tcg tcg ctg ccc ctg tcc ctg ctg         102
Ser Gly Gln Val Arg Pro Leu Pro Ser Ser Leu Pro Leu Ser Leu Leu
         10                  15                  20 ctg ctc ctc ctc ctg tgc tgc tcc ggc acc tcg tgg gga tgg agc acg         150
Leu Leu Leu Leu Leu Cys Cys Ser Gly Thr Ser Trp Gly Trp Ser Thr
     25                  30                  35 tcc cgg gga gga gcc gcc agg gag tgc ggc ttc gat ggc aag ctg gag         198
Ser Arg Gly Gly Ala Ala Arg Glu Cys Gly Phe Asp Gly Lys Leu Glu
 40                  45                  50                  55 gcc ctg gag ccg cgc cac aag gtg cag tct gag gcc ggc tcc gtc cag         246
Ala Leu Glu Pro Arg His Lys Val Gln Ser Glu Ala Gly Ser Val Gln
                 60                  65                  70 tac ttc agc cgg ttc aac gaa gcc gac cgg gag ctc acc tgc gcc ggc         294
Tyr Phe Ser Arg Phe Asn Glu Ala Asp Arg Glu Leu Thr Cys Ala Gly
             75                  80                  85 atc ttc gcc gtc cgc gtc gtc gtc gac gcc atg ggc ctc ctg ctc cct         342
Ile Phe Ala Val Arg Val Val Val Asp Ala Met Gly Leu Leu Leu Pro
         90                  95                 100 cga tac tcc aac gtc cat tcg ctt gtc tac atc gtc caa ggg aga ggg         390
Arg Tyr Ser Asn Val His Ser Leu Val Tyr Ile Val Gln Gly Arg Gly
     105                 110                 115 atc att ggg ttc tcg ttt ccg gga tgc caa gag gag acc cag cag cag         438
Ile Ile Gly Phe Ser Phe Pro Gly Cys Gln Glu Glu Thr Gln Gln Gln
120                 125                 130                 135 cag tat gga tac gga tat gga tat gga cac cat cac cag cat gac             486
Gln Tyr Gly Tyr Gly Tyr Gly Tyr Gly His His His Gln His Asp
                 140                 145                 150 cac cac aag atc cac cga ttc gag cag ggc gac gtg gtg gcc atg ccg         534
His His Lys Ile His Arg Phe Glu Gln Gly Asp Val Val Ala Met Pro
             155                 160                 165 gcc ggc gcc cag cac tgg ctg tac aac gac ggc gac gcg ccg ctt gtg         582
Ala Gly Ala Gln His Trp Leu Tyr Asn Asp Gly Asp Ala Pro Leu Val
         170                 175                 180 gcg gtc tac gtc ttc gac gag aac aac aac atc aac cag ctc gag cct         630
Ala Val Tyr Val Phe Asp Glu Asn Asn Asn Ile Asn Gln Leu Glu Pro
     185                 190                 195 tcc atg agg aaa ttt ttg ctg gct ggg ggc ttc agc aag ggg cag ccc         678
Ser Met Arg Lys Phe Leu Leu Ala Gly Gly Phe Ser Lys Gly Gln Pro
200                 205                 210                 215 cac ttc gcc gag aac atc ttc aaa ggg atc gac gcc cgg ttc ctg agc         726
His Phe Ala Glu Asn Ile Phe Lys Gly Ile Asp Ala Arg Phe Leu Ser
                 220                 225                 230 gaa gcc ctg ggc gtc agc atg cac gtc gcc gag aag ctg cag agc cgg         774
Glu Ala Leu Gly Val Ser Met His Val Ala Glu Lys Leu Gln Ser Arg
             235                 240                 245 cgt gac cag cga ggc gag atc gtc cgc gtg gag ccg gag cac ggc ttt         822
Arg Asp Gln Arg Gly Glu Ile Val Arg Val Glu Pro Glu His Gly Phe
         250                 255                 260 cac cag ctg aat ccg tcg ccg tcg tcg tcg ttt tcg ttc cca tcg             870
His Gln Leu Asn Pro Ser Pro Ser Ser Ser Phe Ser Phe Pro Ser
     265                 270                 275
```

-continued

| | |
|---|---|
| tca caa gtc cag tac caa acg tgc cag cgc gac gtc gac agg cac aac<br>Ser Gln Val Gln Tyr Gln Thr Cys Gln Arg Asp Val Asp Arg His Asn<br>280                   285                290                295 | 918 |
| gtc tgc gcc atg gag gtg agg cac agc gtc gaa cgg ctg gac cag gcc<br>Val Cys Ala Met Glu Val Arg His Ser Val Glu Arg Leu Asp Gln Ala<br>                      300                305                310 | 966 |
| gac gtc tac agc cct ggg gct ggg agg atc aca cgc ctc acc agc cac<br>Asp Val Tyr Ser Pro Gly Ala Gly Arg Ile Thr Arg Leu Thr Ser His<br>              315                320                325 | 1014 |
| aag ttc ccc gtc ctc aac ctc gta cag atg agc gcg gtg cgg gta gac<br>Lys Phe Pro Val Leu Asn Leu Val Gln Met Ser Ala Val Arg Val Asp<br>330                    335                340 | 1062 |
| ctg tac cag gac gcc atc atg tcg ccg ttc tgg aac ttc aac gcc cac<br>Leu Tyr Gln Asp Ala Ile Met Ser Pro Phe Trp Asn Phe Asn Ala His<br>    345                350                355 | 1110 |
| agc gcc atg tac ggc atc agg ggc agt gca agg gtc cag gtc gcc agc<br>Ser Ala Met Tyr Gly Ile Arg Gly Ser Ala Arg Val Gln Val Ala Ser<br>360                    365                370                375 | 1158 |
| gac aac ggg acc acg gtg ttc gac gac gtg ctc cgt gcg ggg cag ctg<br>Asp Asn Gly Thr Thr Val Phe Asp Asp Val Leu Arg Ala Gly Gln Leu<br>                      380                385                390 | 1206 |
| ctc atc gta ccc cag ggc tac ctc gtc gcc acc aag gcg cag gga gaa<br>Leu Ile Val Pro Gln Gly Tyr Leu Val Ala Thr Lys Ala Gln Gly Glu<br>              395                400                405 | 1254 |
| ggc ttc cag tac atc gcc ttc gag acg aac cct gac acc atg gtc agc<br>Gly Phe Gln Tyr Ile Ala Phe Glu Thr Asn Pro Asp Thr Met Val Ser<br>            410                415                420 | 1302 |
| cac gtc gcc ggg aag aac tcc gtc ctg agc gac ttg ccg gcc gcc gtc<br>His Val Ala Gly Lys Asn Ser Val Leu Ser Asp Leu Pro Ala Ala Val<br>425                    430                435 | 1350 |
| atc gcc agc tcg tat gcc atc tcc atg gag gaa gct gca gag ctc aag<br>Ile Ala Ser Ser Tyr Ala Ile Ser Met Glu Glu Ala Ala Glu Leu Lys<br>440                    445                450                455 | 1398 |
| aac ggt agg aag cat gag ctg gct gtg ctt act cct gct ggc agt ggc<br>Asn Gly Arg Lys His Glu Leu Ala Val Leu Thr Pro Ala Gly Ser Gly<br>                      460                465                470 | 1446 |
| agc tac caa caa ggt caa gct ggc agc gcc caa cag taggcacaac<br>Ser Tyr Gln Gln Gly Gln Ala Gly Ser Ala Gln Gln<br>475                    480 | 1492 |
| ctcagagtga tctgcctgaa taagtactcg tagactgtaa taattaaaca aagcttgctc | 1552 |
| atggttaaac tgcgtgttga ttagtctttc aactacatag ctctaaagtt tttgatacac | 1612 |
| cgagtgattt gccagggaaa aaatgagcag attgttgtaa gc | 1654 |

<210> SEQ ID NO 5
<211> LENGTH: 483
<212> TYPE: PRT
<213> ORGANISM: Zea mays

<400> SEQUENCE: 5

Met Ala Ala Ala Ile Val Leu Ser Gly Gln Val Arg Pro Leu Pro Ser
  1                   5                   10                15

Ser Leu Pro Leu Ser Leu Leu Leu Leu Leu Leu Cys Cys Ser Gly
                 20                   25                 30

Thr Ser Trp Gly Trp Ser Thr Ser Arg Gly Gly Ala Ala Arg Glu Cys
                35                   40                 45

Gly Phe Asp Gly Lys Leu Glu Ala Leu Glu Pro Arg His Lys Val Gln
    50                 55                 60

Ser Glu Ala Gly Ser Val Gln Tyr Phe Ser Arg Phe Asn Glu Ala Asp

```
            65                  70                  75                  80
Arg Glu Leu Thr Cys Ala Gly Ile Phe Ala Val Arg Val Val Asp
                    85                  90                  95
Ala Met Gly Leu Leu Pro Arg Tyr Ser Asn Val His Ser Leu Val
                    100                 105                 110
Tyr Ile Val Gln Gly Arg Gly Ile Ile Gly Phe Ser Phe Pro Gly Cys
                115                 120                 125
Gln Glu Glu Thr Gln Gln Gln Tyr Gly Tyr Gly Tyr Gly Tyr Gly
            130                 135                 140
His His His His Gln His Asp His His Lys Ile His Arg Phe Glu Gln
145                 150                 155                 160
Gly Asp Val Val Ala Met Pro Ala Gly Ala Gln His Trp Leu Tyr Asn
                        165                 170                 175
Asp Gly Asp Ala Pro Leu Val Ala Val Tyr Val Phe Asp Glu Asn Asn
                    180                 185                 190
Asn Ile Asn Gln Leu Glu Pro Ser Met Arg Lys Phe Leu Leu Ala Gly
                195                 200                 205
Gly Phe Ser Lys Gly Gln Pro His Phe Ala Glu Asn Ile Phe Lys Gly
            210                 215                 220
Ile Asp Ala Arg Phe Leu Ser Glu Ala Leu Gly Val Ser Met His Val
225                 230                 235                 240
Ala Glu Lys Leu Gln Ser Arg Arg Asp Gln Arg Gly Glu Ile Val Arg
                        245                 250                 255
Val Glu Pro Glu His Gly Phe His Gln Leu Asn Pro Ser Pro Ser Ser
                260                 265                 270
Ser Ser Phe Ser Phe Pro Ser Ser Gln Val Gln Tyr Gln Thr Cys Gln
            275                 280                 285
Arg Asp Val Asp Arg His Asn Val Cys Ala Met Glu Val Arg His Ser
            290                 295                 300
Val Glu Arg Leu Asp Gln Ala Asp Val Tyr Ser Pro Gly Ala Gly Arg
305                 310                 315                 320
Ile Thr Arg Leu Thr Ser His Lys Phe Pro Val Leu Asn Leu Val Gln
                        325                 330                 335
Met Ser Ala Val Arg Val Asp Leu Tyr Gln Asp Ala Ile Met Ser Pro
                340                 345                 350
Phe Trp Asn Phe Asn Ala His Ser Ala Met Tyr Gly Ile Arg Gly Ser
            355                 360                 365
Ala Arg Val Gln Val Ala Ser Asp Asn Gly Thr Thr Val Phe Asp Asp
            370                 375                 380
Val Leu Arg Ala Gly Gln Leu Leu Ile Val Pro Gln Gly Tyr Leu Val
385                 390                 395                 400
Ala Thr Lys Ala Gln Gly Glu Gly Phe Gln Tyr Ile Ala Phe Glu Thr
                    405                 410                 415
Asn Pro Asp Thr Met Val Ser His Val Ala Gly Lys Asn Ser Val Leu
                420                 425                 430
Ser Asp Leu Pro Ala Ala Val Ile Ala Ser Ser Tyr Ala Ile Ser Met
            435                 440                 445
Glu Glu Ala Ala Glu Leu Lys Asn Gly Arg Lys His Glu Leu Ala Val
        450                 455                 460
Leu Thr Pro Ala Gly Ser Gly Ser Tyr Gln Gln Gly Gln Ala Gly Ser
465                 470                 475                 480
Ala Gln Gln
```

<210> SEQ ID NO 6
<211> LENGTH: 36
<212> TYPE: DNA
<213> ORGANISM: Artificial Sequence
<220> FEATURE:
<223> OTHER INFORMATION: Zm-Leg1 Promoter Primer 362

<400> SEQUENCE: 6
aagcttgata tcgagtcagg tcaacttggc caaact                    36

<210> SEQ ID NO 7
<211> LENGTH: 42
<212> TYPE: DNA
<213> ORGANISM: Artificial Sequence
<220> FEATURE:
<223> OTHER INFORMATION: Zm-Leg1 Promoter Primer 363

<400> SEQUENCE: 7
ggatcccggg ccatggcagc gctgcctctg ctcgctcgct ca             42

<210> SEQ ID NO 8
<211> LENGTH: 37
<212> TYPE: DNA
<213> ORGANISM: Artificial Sequence
<220> FEATURE:
<223> OTHER INFORMATION: Zm-Leg1B Promoter Primer 364

<400> SEQUENCE: 8
aagcttgata tcttgttttt ctgacaaatg gttgctc                   37

<210> SEQ ID NO 9
<211> LENGTH: 42
<212> TYPE: DNA
<213> ORGANISM: Artificial Sequence
<220> FEATURE:
<223> OTHER INFORMATION: Zm-Leg1B Promoter Primer 365

<400> SEQUENCE: 9
ggatcccggg ccatggcagc gctgcctctg ctcgctcgct ca             42

<210> SEQ ID NO 10
<211> LENGTH: 26
<212> TYPE: DNA
<213> ORGANISM: Artificial Sequence
<220> FEATURE:
<223> OTHER INFORMATION: Zm-Leg1 Terminator Primer 163

<400> SEQUENCE: 10
ggatccgcac aacctcagag tgatct                               26

<210> SEQ ID NO 11
<211> LENGTH: 27
<212> TYPE: DNA
<213> ORGANISM: Artificial Sequence
<220> FEATURE:
<223> OTHER INFORMATION: Zm-Leg1 Terminator Primer 164

<400> SEQUENCE: 11 gggcccccagt ataactatgc cgaggtt                             27

<210> SEQ ID NO 12
<211> LENGTH: 26
<212> TYPE: DNA
<213> ORGANISM: Artificial Sequence
<220> FEATURE:
<223> OTHER INFORMATION: LEG1 PRO GSP1

```
<400> SEQUENCE: 12
agccggcctc agactgcacc ttgtgg                                          26

<210> SEQ ID NO 13
<211> LENGTH: 27
<212> TYPE: DNA
<213> ORGANISM: Artificial Sequence
<220> FEATURE:
<223> OTHER INFORMATION: LEG1 PRO GSP2

<400> SEQUENCE: 13
cgcacctggc cggagagtac tattgcc                                         27

<210> SEQ ID NO 14
<211> LENGTH: 25
<212> TYPE: DNA
<213> ORGANISM: Artificial Sequence
<220> FEATURE:
<223> OTHER INFORMATION: LEG1 TERM GSP1

<400> SEQUENCE: 14
agtaggcaca acctcagagt gatct                                           25

<210> SEQ ID NO 15
<211> LENGTH: 25
<212> TYPE: DNA
<213> ORGANISM: Artificial Sequence
<220> FEATURE:
<223> OTHER INFORMATION: LEG1 TERM GSP2

<400> SEQUENCE: 15
ttaaacaaag cttgctcatg gttaa                                           25
```